United States Patent
Thomson et al.

(10) Patent No.: US 9,111,024 B2
(45) Date of Patent: Aug. 18, 2015

(54) MEDICAL TREATMENT MANAGEMENT DEVICE, METHOD, AND PROGRAM FOR TRACKING AND ADVISING PATIENT CAREGIVERS

(75) Inventors: Chris M. Thomson, Lynchburg, VA (US); Chad Hoyt, Lynchburg, VA (US)

(73) Assignee: ART OF HEALTHCARE, LLC, Lynchburg, VA (US)

( * ) Notice: Subject to any disclaimer, the term of this patent is extended or adjusted under 35 U.S.C. 154(b) by 428 days.

(21) Appl. No.: 13/584,058

(22) Filed: Aug. 13, 2012

(65) Prior Publication Data

US 2014/0046940 A1    Feb. 13, 2014

(51) Int. Cl.
G06F 7/00    (2006.01)
G06F 17/30    (2006.01)
G06F 19/00    (2011.01)

(52) U.S. Cl.
CPC ................................. G06F 19/3418 (2013.01)

(58) Field of Classification Search
None
See application file for complete search history.

(56) References Cited

U.S. PATENT DOCUMENTS

| | | | |
|---|---|---|---|
| 5,808,376 A * | 9/1998 | Gordon et al. | 307/66 |
| 2003/0092976 A1* | 5/2003 | Murase et al. | 600/300 |
| 2007/0130206 A1* | 6/2007 | Zhou et al. | 707/104.1 |
| 2007/0194939 A1* | 8/2007 | Alvarez et al. | 340/573.1 |
| 2008/0200824 A1* | 8/2008 | Kane et al. | 600/532 |
| 2010/0179820 A1* | 7/2010 | Harrison et al. | 705/2 |
| 2010/0228699 A1* | 9/2010 | Webber et al. | 707/622 |
| 2011/0004110 A1* | 1/2011 | Shusterman | 600/509 |
| 2012/0046962 A1* | 2/2012 | Fant | 705/2 |
| 2012/0117099 A1* | 5/2012 | Gross | 707/758 |
| 2012/0136882 A1* | 5/2012 | Kawagishi et al. | 707/758 |
| 2013/0268286 A1* | 10/2013 | Flores et al. | 705/2 |
| 2013/0311466 A1* | 11/2013 | Classen | 707/736 |

* cited by examiner

Primary Examiner — Hexing Liu
(74) Attorney, Agent, or Firm — Oliff PLC (57) ABSTRACT

A portable medical treatment device is designed to be placed on or near a patient when the patient is moved. The device communicates with a database that stores patient profiles and/or treatment protocols. Based on input patient information, the device communicates with the database and loads a patient profile and/or treatment protocol. The device evaluates data entered by a user according the patient profile and/or treatment protocol to determine metrics, and the determined metrics are compared with parameters to determine whether the entered data is within acceptable limits. The device tags and displays the entered data in a manner that reflects whether it was within the acceptable limits.

24 Claims, 6 Drawing Sheets

MEDICAL TREATMENT MANAGEMENT DEVICE, METHOD, AND PROGRAM FOR TRACKING AND ADVISING PATIENT CAREGIVERS

BACKGROUND

Portable medical devices are known that allow individuals to contact healthcare providers in emergencies. These devices generally include a button that allows a wearer to alert emergency medical personnel if they experience a medical emergency and are unable to reach a telephone.

Hospitals and other healthcare establishments utilize software databases to track patient treatment and keep patient records. The electronic health record (EHR) is one such database system that is commonly used. Sometime after a patient has been treated, the caregiver or some other staff member will update the patient's records in the EHR for recordkeeping and billing purposes.

SUMMARY

Emergency systems of care require rapid transitions from one care component to the next. Seconds and minutes literally matter. Representative examples of these time-sensitive processes include acute myocardial infarction, acute stroke, and sepsis. As a patient experiencing an acute myocardial infarction progresses through the care system from home to ambulance to emergency department to cardiac catheterization lab, critical steps occur that must occur smoothly and quickly.

Time interval "best practice" targets have been strictly defined by regulatory bodies (American Heart Association, American Stroke Association, and Joint Commission, among others). Disease-specific certifications are awarded to high performing organizations based on meeting or exceeding, these standards, and it is evident these high performing organizations deliver better health outcomes to patients with these diseases.

Optimizing medical processes requires diligence, dedicated process improvement methods, and detailed data, including accurate times within the care intervals and identification and characterization of process breakdowns, when they occur.

As discussed above, the EHR, is only updated at some point after a patient has been treated. Thus, the EHR inadequately represents what is happening in real time because many, if not most, of the timestamps in the EHR are added after the treatment has occurred. Furthermore, the EHR cannot effectively document any malfunctions and/or barriers to successful completion of a treatment step in any given situation. Because the EHR is used for so many purposes, the ERR also has many documentation requirements aside from the important data specific to the clinical presentation that inhibit its ability to provide timely and useful information that can meaningfully influence treatment in a timely manner. For these reasons, when a process breakdown occurs, it cannot be adequately or reliably documented for purposes of improving the treatment process and affecting caregiver behavior in a positive manner.

Thus, there is a need for a portable medical device that can remain with a patient and allows various healthcare providers to immediately input relevant information regarding the patients treatment without requiring unnecessary information, and also immediately provide useful information and/or instructions regarding the patient's condition and treatment to the healthcare professionals in real time to ensure that the patient is efficiently and effectively treated.

A portable device is needed to identify a patient as involved in a pre-determined, time sensitive care process. The device remains with the patient so that each caregiver immediately knows what the patient's condition is, exactly what has been done, the timing of what has been done, and what still needs to be done. Furthermore, the device can evaluate metrics (such as timing) so that the caregiver can see whether anything occurred outside of preferable parameters.

Exemplary embodiments of the broad inventive principles described herein provide a portable medical treatment device that can be placed on or near a patient when the patient is moved. The device communicates with a database that stores patient profiles and/or treatment protocols. Based on input, patient information, the device communicates with the database and loads a patient profile and/or treatment protocol. The device evaluates data entered by a user according the patient profile and/or treatment protocol to determine metrics, and the determined metrics are compared with parameters to determine whether the entered data is within acceptable limits. The device tags and displays the entered data in a manner that reflects whether it was within the acceptable limits.

According to exemplary embodiments, based on the data entered by the user, the device can also determine whether any treatment errors or unforeseen events (herein termed "malfunctions") have occurred that might require adjustment of a treatment protocol.

According to exemplary embodiments the data collected, including the metrics and/or tags can be uploaded to the database for statistical analysis to improve the stored patient profile and/or treatment protocols.

BRIEF DESCRIPTION OF THE DRAWINGS

Exemplary embodiments now be described with reference to the accompanying drawings, wherein.

DETAILED DESCRIPTION OF EMBODIMENTS

Embodiments of the medical treatment device according to the invention will be described with reference to FIGS. 1-3. In general, the embodiments described below provide portable medical treatment devices that input, evaluate, and store patient profile data to select a particular treatment protocol. The medical treatment devices output instructions regarding the particular protocol, and receive data input indicative of information gathered while the protocol is being performed. This, way a practitioners using the device can both effectively collect patient data during treatment in a centralized location, but also can receive useful treatment protocol information based on the information collected. Furthermore, if the devices detect any abnormality in the data being, collected, the devices can adjust the treatment protocol to account for the abnormality. After treatment is complete, data can be sent from the devices to a centralized database for analysis to evaluate the quality of treatment and adjust protocols to increase the quality of treatment.

Figure 1:
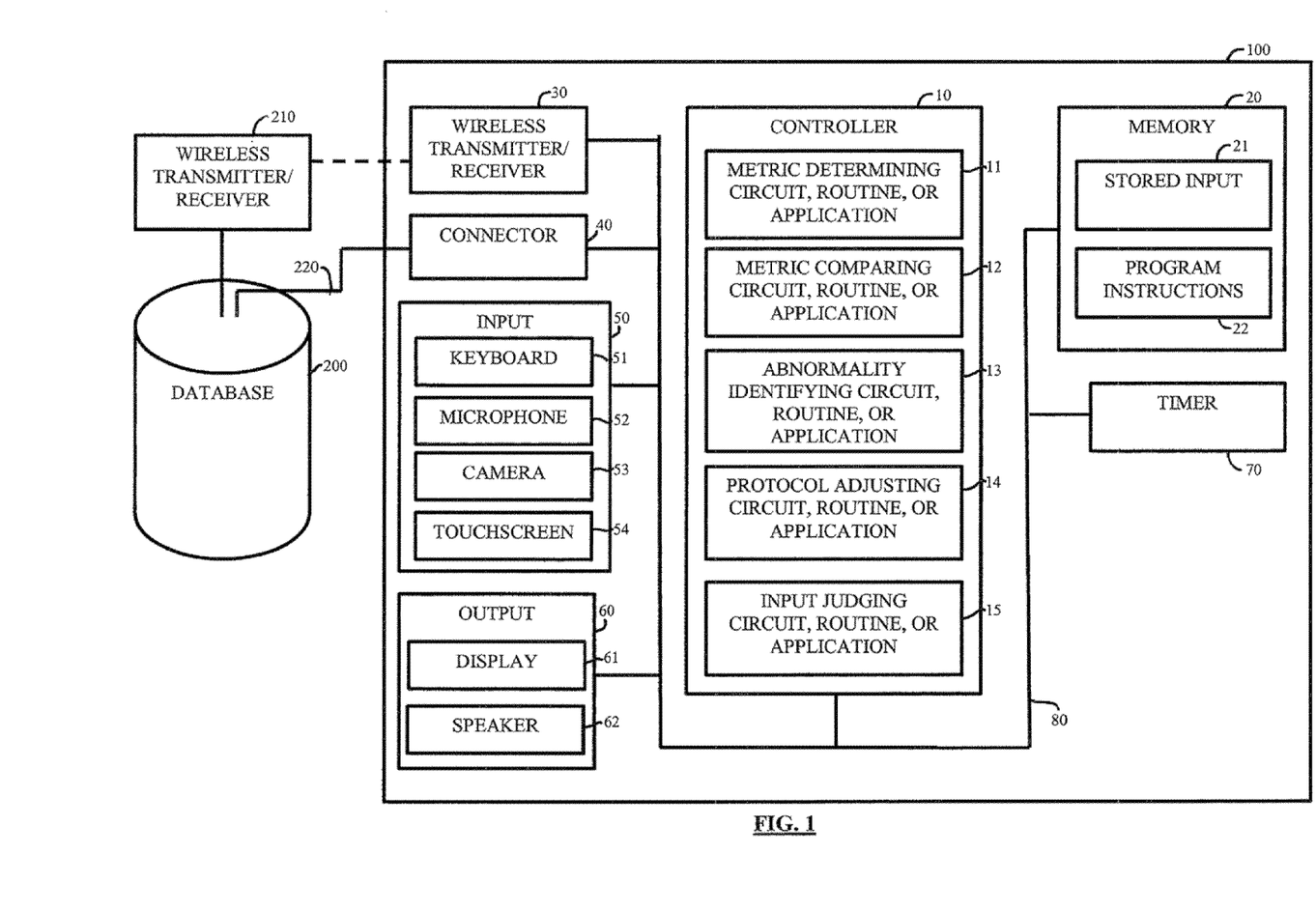
FIG. 1 schematically shows an example of a medical treatment device.

FIG. 1 shows an embodiment of a medical device 100. The medical treatment device is a portable computer-type device that can be associated with a patient and that is capable of accessing data and storing data in a local or remote database. Thus, the medical device may be implemented, for example, in the form of a portable computer, tablet computer, smartphone, handheld device, or any other portable device capable of receiving input data, storing data, operating on the input/ and, or stored data, accessing a database (either local or remote), and outputting data. As shown in FIG. 1, according to this embodiment, the medical treatment device 100 includes a controller 10, a memory 20, a wireless transmitter/ receiver 30, a connector 40, an input section 50, an output section 60, a timer 70, and an internal communication bus 80, each of which will be described in more detail below.

The controller 10 controls the flow of data within the medical treatment device 100 and also performs various operations on the data by implementing one or more circuits, routines, or applications. The controller may be configured as a central processing unit (CPU) that implements program routines and/ or applications stored in a memory to achieve its functions, a collection of discrete purpose-programmed circuits, and or a combination of both. According to this embodiment, the controller 10 is physically, functionally, and/or conceptually divided into a metric determining circuit, routine, or application 11, a metric comparing circuit, routine, or application 12, an abnormality identifying circuit, routine or application 13, a protocol adjusting circuit, routine, or application 14, and an input judging circuit, routine, or application 15.

The metric determining circuit, routine, or application 11 evaluates input data and extracts from the input data a relevant metric. As used herein the term "metric" refers to a particular measurable quantity that can be compared with an ideal value, range, or pattern. Some examples of metrics include, elapsed time, heart rate, blood pressure. EKG, blood oxygen saturation, blood sugar level, etc.

The metric comparing circuit, routine, or application 12 compares metric data with parameter data for the particular metric to determine whether or not the particular metric falls within or is outside of the parameter data. For example, if a particular metric was heart rate of 150 beats per minute (bpm) and the parameter data for heart rate was 50-130 bpm. The metric comparing circuit, routine, or application 12 would compare the metric of 150 bpm with the parameter data of 50-130 bpm and determine that the metric was outside the parameter data.

The abnormality identifying circuit, routine, or application 13 evaluates input data to determine whether or not there is an abnormality. For example, when data is entered in accordance with particular treatment protocol, the abnormality identifying circuit, routine, or application 13 checks the input data to determine if something abnormal to the treatment protocol has occurred. For example, if a patient's blood pressure has risen after a previous protocol data entry indicated the administration of blood-pressure-reducing medication, an abnormality would be identified.

The protocol adjusting circuit, routine, or application 14 can adjust a particular treatment protocol in response to an indication of an abnormality. Returning to the above example, if an abnormality indicating that a patient's blood, pressure has risen after a previous protocol data entry indicated the administration of a blood-pressure-reducing medication is identified, the protocol adjusting circuit, routine, or application 14 could adjust the protocol to account for the increased blood pressure by including additional blood-pressure-reducing measures as part of the adjusted protocol.

The input judging circuit, routine, or application 15 judges inputs received by the input section 50 and determines whether the input is acceptable. If the input is unacceptable, the input judging circuit, routine, or application 15 outputs an error message and suggests re-entry of the data determined to be unacceptable.

The memory 20 can be composed of one or more internal and/or removable, volatile, and/or non-volatile computer-readable storage mediums, such as for example, a RAM, a ROM, a flash memory, an internal optical drive, a solid-state drive, etc. As used herein, the term "computer-readable storage medium" is not intended to encompass transitory carrier waves. The memory 20 can be physically, functionally, and/or conceptually divided into a stored input section 21 and a program instructions section 22. The stored input section 21 stores data that is input via the input 50. The program instructions section 22 can include program instructions to implement all or part of one or more of the circuits, routines, or applications in the controller 10.

The wireless transmitter/receiver 30 is capable of communicating wirelessly with other devices. The wireless transmitter receiver 30 may be configured to communicate over one or more of Wi-Fi, a cellular telephone network, Bluetooth®, and/or by any other wireless means.

The connector 40 provides a wired connection between the medical treatment device 100 and other devices. The connector 40 can include a port permitting the connection of a cable 220 directly or through a dock designed for the medical treatment device 100.

The input 50 includes one or more devices capable of receiving input, such as a keyboard 51, a microphone 52, a camera 53, and/or a touchscreen 54. The keyboard 51 may be composed of keys or may be a touchscreen keyboard on the touchscreen 54. Input received via the microphone can be converted into text before being stored in the stored input section 21 by a conventional speech recognition program stored in the program instructions 22 section of the memory 20 and executed by the controller 10. The camera 53 may be a digital camera.

The output 60 includes one or more devices capable of outputting information to the user. The output 60 can include a display 61 and/or a speaker 62. The display 61 may be a liquid crystal display, an electronic paper display, or any other display capable of displaying information. The display 61 may incorporate the touchscreen 54. The speaker 62 can output audible instructions or a preferred timing based on a treatment protocol, such as "you have five minutes to complete this task," or "if the results of test X are outside of range Y, proceed immediately to Z."

The tinier 70 includes a dock, calendar, and/or a stopwatch-type timer that can be used to determine the time and date at which data is entered and the elapsed time between different entries. In most cases, timing will be a relevant metric. The internal communication bus 80 includes one or more electrical or fiber-optic connections that allow the various components within the medical treatment device 100 to communicate with one another.

According to this embodiment, the medical treatment device 100 is connectable to a database 200 by at least one of the wireless transmitter/receiver 30 and the connector 40. The connector 40 can connect to the database 200 using a cable 220. The wireless transmitter/receiver 30 can connect to the database via, a wireless transmitter/receiver 210 connected to the database 200. The database 200 stores various patient profiles and treatment protocols that can be downloaded by the medical treatment device 100.

The patient profiles include various questions designed to gather information about a patient's medical condition and preliminary treatment. Each patient profile is designed to be used for one or more particular medical conditions. Thus, each patient profile is stored in the database in a manner in which it can be retrieved based on information identifying a corresponding medical condition. Such identifying information could include the name of the medical condition, or one or more symptoms associated with the medical condition. The patient profiles can include, for example, questions about the timing of certain events, such as what time the patient experienced symptoms, what time emergency personnel arrived, what time the patient arrived at the hospital, etc. The patient profiles can include, for example, questions about symptoms, preliminary tests, and treatment, such as for example, what symptoms were reported or observed, what types of test were performed by the emergency personnel, and what were the results of the tests. The patient profiles can include, for example, questions about the patient including, identifying information, allergies, health insurance information, etc. Certain generalized patient profiles can be stored that are usable when input information cannot be associated with a specific patient profile.

Each treatment protocol is designed to be used for one or more particular medical conditions. Thus, each treatment protocol is stored in the database in a manner in which it can be retrieved based on information identifying a corresponding medical condition. Such identifying information could include the name of the medical condition, or one or more symptoms associated with the medical condition. The treatment protocols include various treatment instructions and/or events that are associated with a particular medical condition. Each of the instructions and/or events may include sub-instructions aid/or sub-events. For example, a treatment protocol for a heart attack could include treatment milestones such as an EKG, Cath Lab activation, arrival at Cath Lab, Core Drug administration, and Balloon administration. Each of the milestones could include sub-events, possible common malfunctions, and sections for notations to be entered. Certain treatment protocols can be stored that are usable when input information cannot be associated with a specific treatment protocol.

Figure 2:
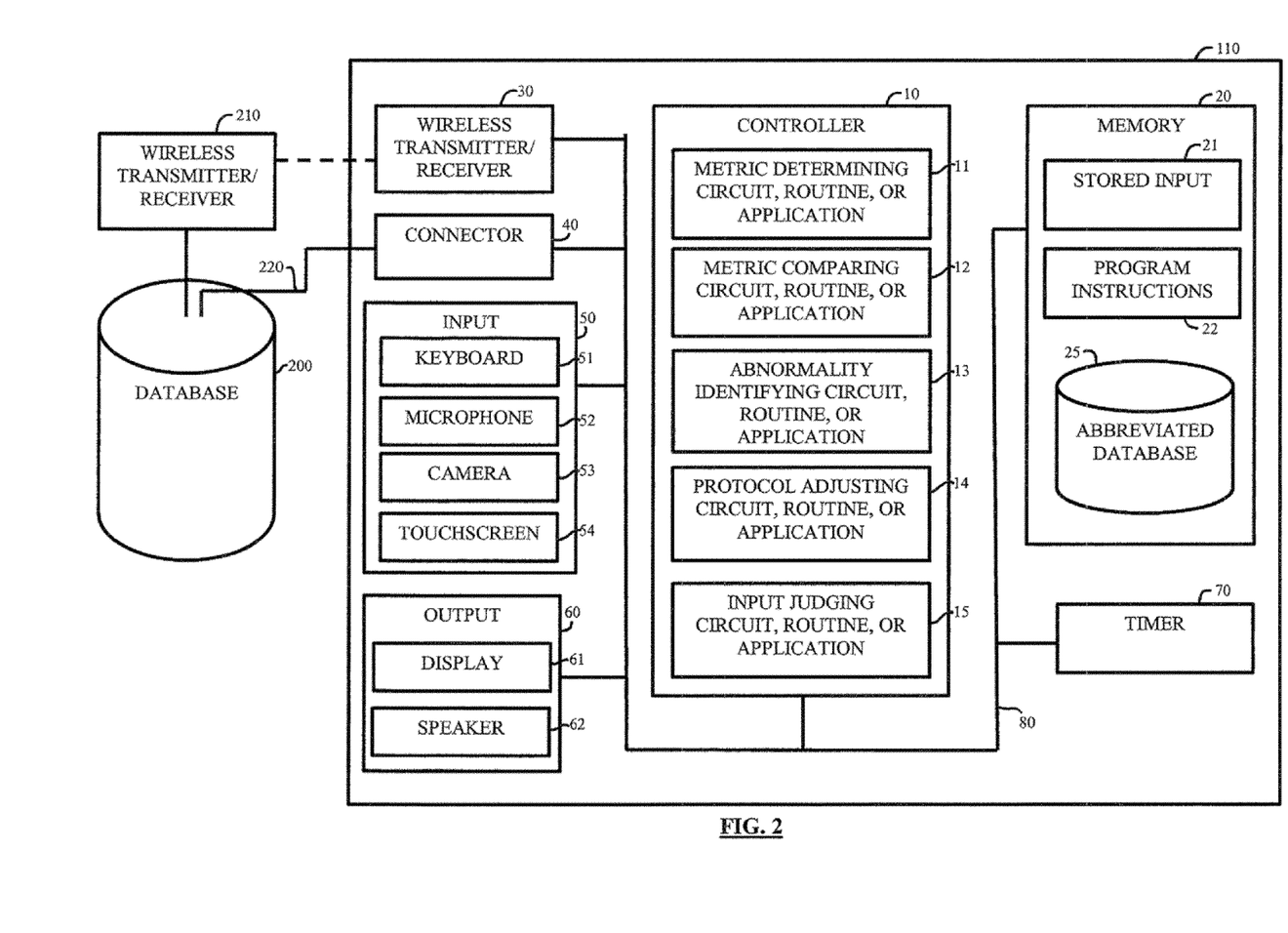
FIG. 2 schematically shows another example of a medical treatment device.

FIG. 2 shows another example of a medical treatment device 110. The medical treatment device 110 is similar to the medical treatment device 100; however, it additionally includes abbreviated database 25. Abbreviated database 25 is an abbreviated version of database 200 that is stored within the medical treatment device 110 and includes the more common patient profiles and treatment protocols. Thus, when the controller 10 of the medical treatment device 110 is unable to access the database 200, for example, because a wireless connection is unavailable, the controller 10 still has access to patient profiles and treatment protocols. This way, the lack of a wireless connection will not prevent the effective use of the medical treatment device 110. Furthermore, the use of abbreviated database 25 requires less memory within the medical treatment device when compared to the entire database 200.

According to this embodiment, the abbreviated database 25 can be updated whenever the medical treatment device 110 is either wirelessly or physically connected to the database 200. Also, according to this embodiment, when a wireless connection is established, the controller can query the database 200 to determine if any patient profiles and/or treatment protocols that are more relevant to a patient's condition are stored in the database 200.

Figure 3:
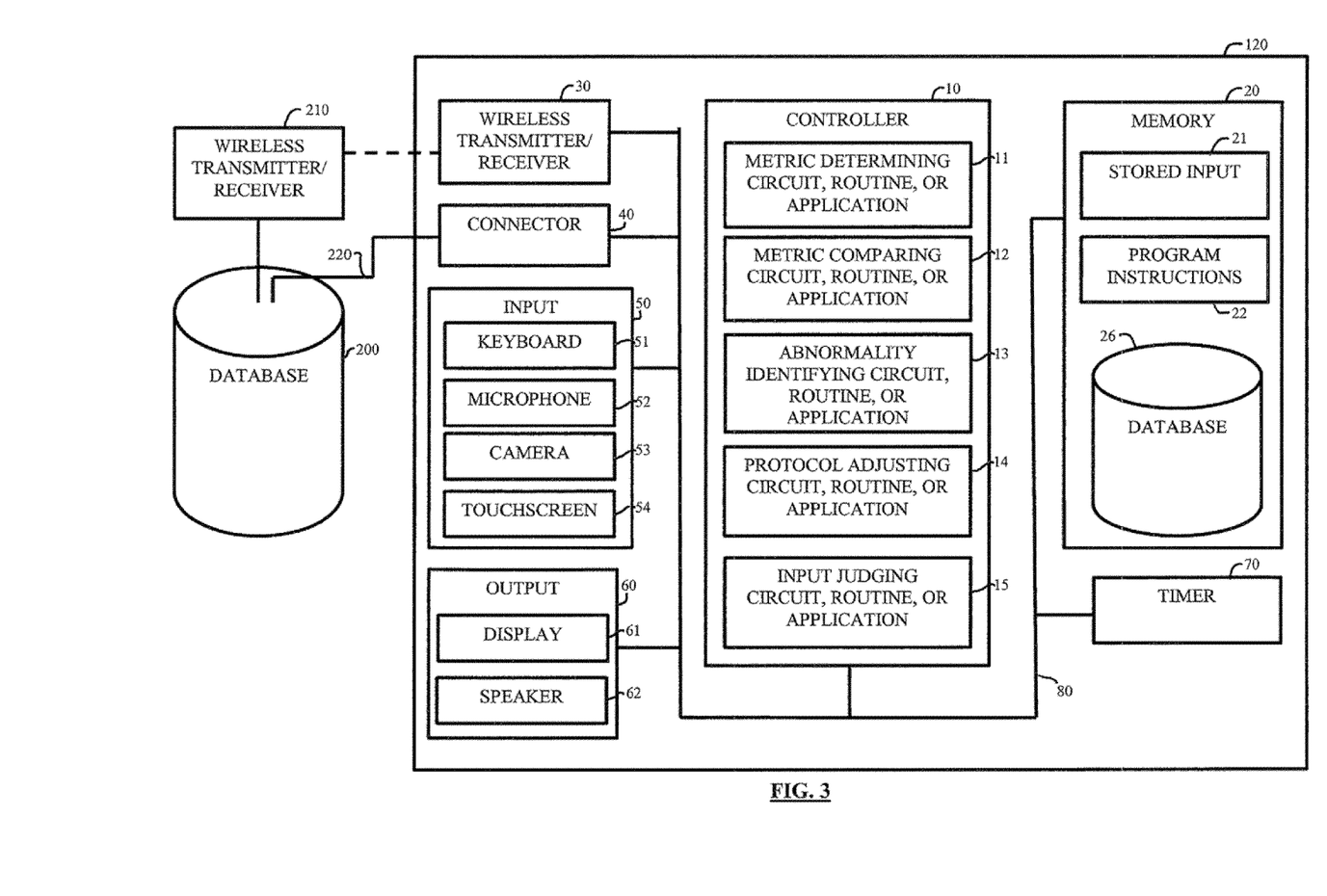
FIG. 3 schematically shows another example of a medical treatment device.

FIG. 3 shows another example of a medical treatment device 120. The medical treatment device 120 is similar to the medical treatment devices 100, 110; however, it includes database 26. Database 26 includes all of the patient profiles and treatment protocols that are stored in database 200. Thus, when the controller 10 of the medical treatment device 120 is unable to access the database 200, for example, because a wireless connection is unavailable, the controller 10 still has access to all of the patient profiles and treatment protocols. This way, the lack of a wireless connection will allow equally effective use of the medical treatment device 120. That is, there is no risk that a less relevant patient profile and/or treatments protocol will have to be used because the database 26 is not abbreviated. According to this embodiment, the database 26 can be updated whenever the medical treatment device 120 is either wirelessly or physically connected to the database 200.

Figure 4A:
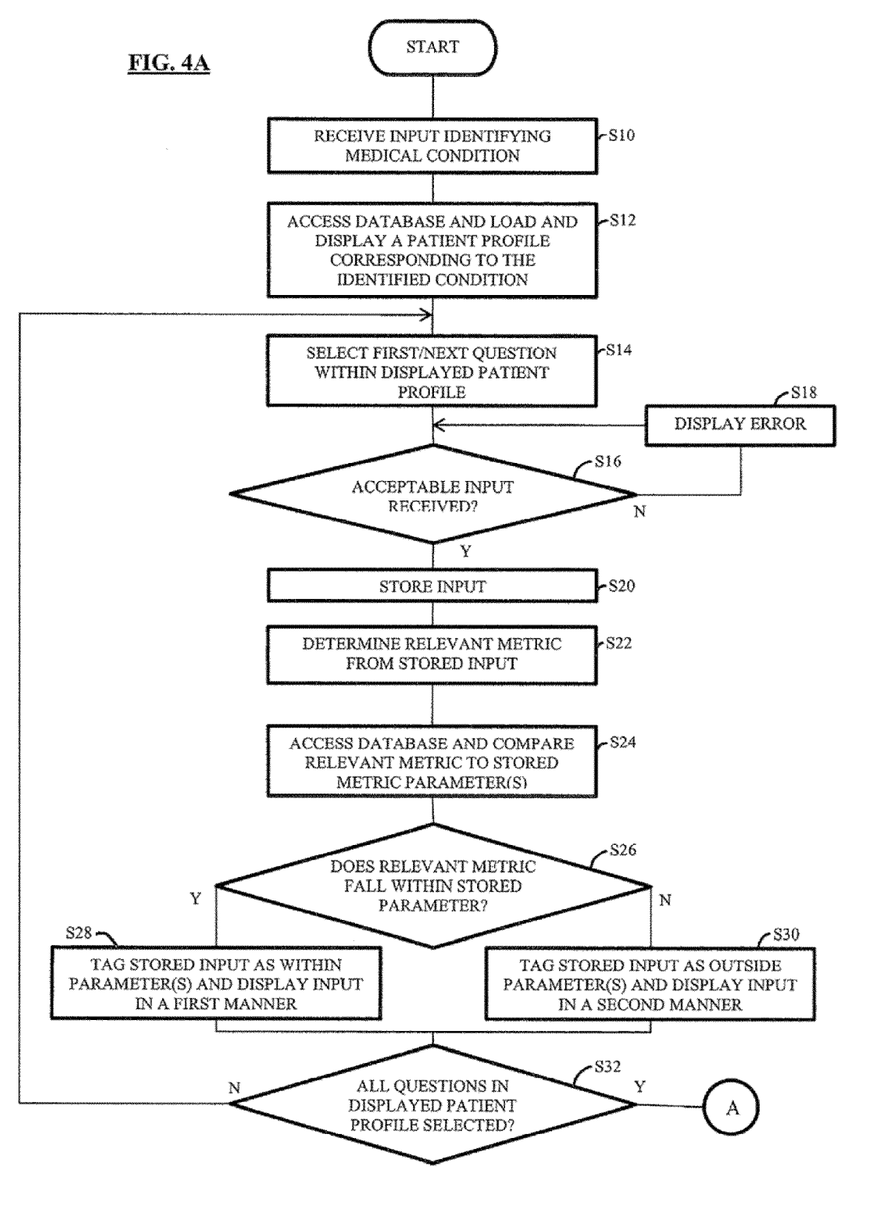
FIGS. 4A and 4B are a flowchart showing an algorithm of an exemplary medical treatment method.
Figure 4B:
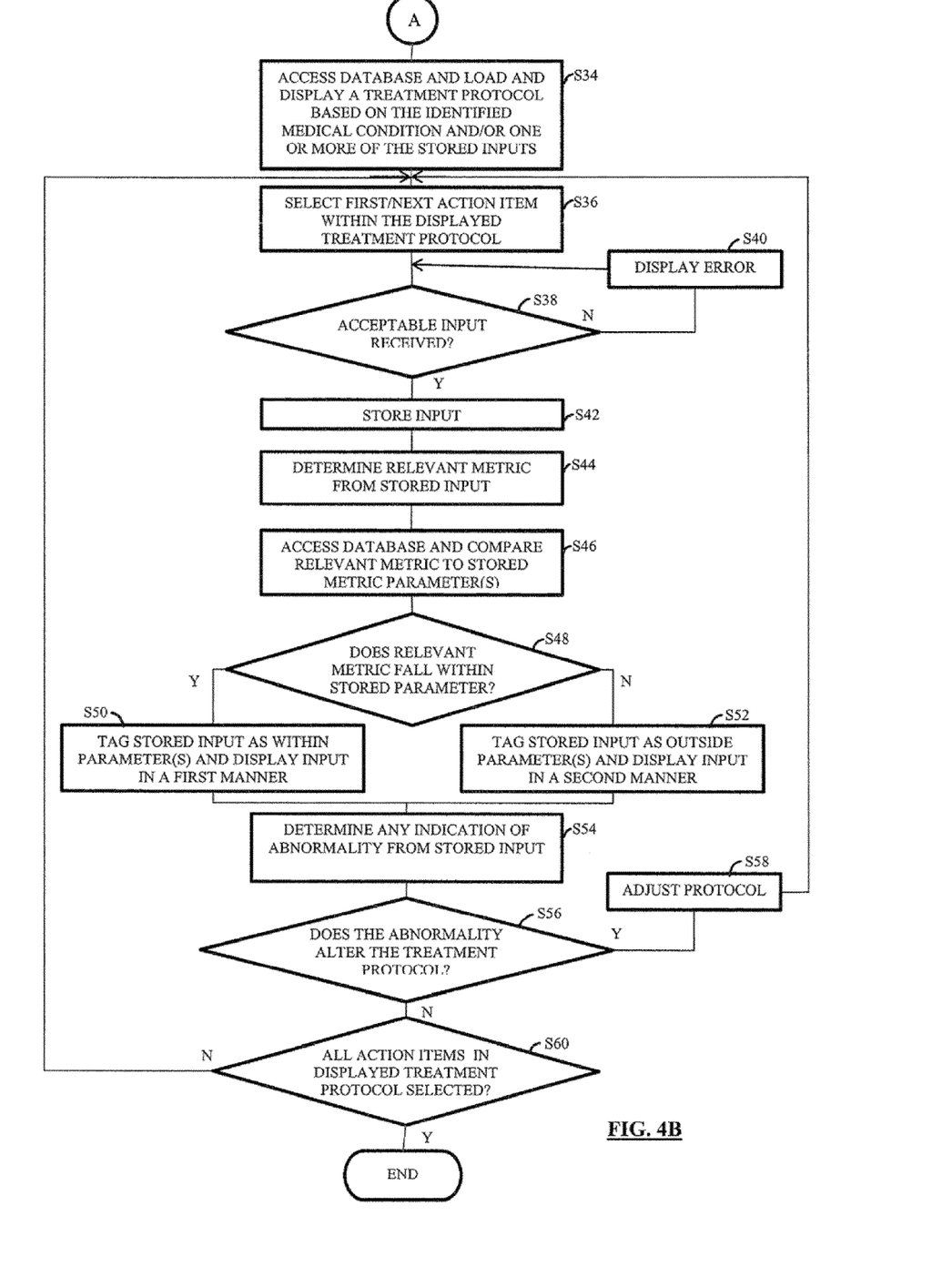

Next, operation of the medical treatment device(s) 100, 110, 120 will be described with reference to a medical treatment method shown in the algorithm in FIGS. 4A and 4B. All or part of the algorithm may be implemented in the form of a computer program that is stored in, for example, one or more computer-readable storage mediums included in the memory 20 of the medical treatment device(s) 100, 110, 120, and executed by the controller 10. Although the method is described in the context of the operation of the above-described medical treatment device(s) 100, 110, 120, the method can be implemented by other devices as well. Thus, the reference to the structure of the medical treatment device(s) 100, 110, 120 should be considered exemplary. That is the method need not be limited by the specific structure of the above-described medical treatment device(s) 100, 110, 120.

The method presupposes that the medical treatment device 100, 110, 120 has been associated with a particular patient. At some point before or during the method, patient identifying information can be optionally entered. Such identifying information could include textual information including, for example, one or more of name, address, social security number, telephone number, physical description, medical record information, allergy information, etc. The identifying information could also include a picture of the patient's face or other identifying feature such as clothing or a fingerprint.

The exemplary method begins by the controller 10 receiving of information usable to identify a particular medical condition of the patient (S10). For example, an operator could input a medical condition and/or patient symptoms into a graphical interface displayed on display 61 via the input 50 using the keyboard 51 and/or the microphone 52. The input condition can be stored in the stored input section 21 of the memory 20 where it can be accessed by the controller 10. Next, by virtue of wireless transmitter/receivers 30, 210, the controller 10 access database 200, and loads a patient profile that corresponds to the input identifying information (S12). According to this example, the patient profile consists of one or more questions that can be used by the medical treatment device 100, 110, 120 to collect important statistical information and identify a treatment protocol.

The controller 10 selects a first question that has been answered within the displayed patient profile (S14) and the input judging circuit, routine, or application 15 determines whether the input answer is acceptable. For example, particular patient profile questions may need to be entered in one or more acceptable formats so that the answer can be properly analyzed. For example, if the first question must be answered with a time and date, a date and/or time in the future, or an answer from which a date and/or time cannot be determined, would be considered to be unacceptable. To help reduce unacceptable answers, displayed data entry fields can be formatted so that answers can only be entered in acceptable formats, or possible answer options could be given in acceptable data formats for simple selection by the user. If an unacceptable input is received (S16=NO), an error is displayed and the data field is cleared (S18).

If an acceptable input is received (S16=YES), the controller 10 stores the input in the stored input portion 21 of the memory 20 (S20) and the metric determining circuit, routine, or application 11 evaluates the input data and determines a relevant metric from the stored input (S22). For example, if the stored input is a time of day of arrival at the hospital, the relevant metric may be an time elapsed between the onset of symptoms and arrival at the hospital. The controller 10 may optionally store the determined metric in the stored input section 21 of the memory 20.

The metric comparing circuit, routine, or application 12 accesses the database 200 and compares the determined metric with stored parameters for the particular metric (S24) to determine whether or not the determined metric falls within the stored parameters (S26). For example, if the relevant metric is a time of 37 minutes elapsed between the onset of symptoms and arrival at the hospital, and the stored parameter for that metric is an interval from zero to thirty minutes, the metric comparing circuit, routine, or application 12 would determine that the metric is outside of the parameter.

If the determined metric is within the stored parameter, the metric comparing circuit, routine, or application 12 tags the stored input from which the metric was determined as being within the parameter and displays the input on the display 61 in a first manner (S28). If the determined metric is outside the stored parameter, the metric comparing circuit, routine, or application 12 tags the stored input as being, outside the perimeter and displays the input on the display 61 the second manner (S29). For example, if the metric was within the parameter, the input may be displayed in a green color on the display 61, and if the metric was outside the parameter, the input may be displayed in a red color on the display 61. Alternatively, emoticons, checks and X's, or any other display methods may be used as long as it can be determined whether or not the metric determined from the input information was within or outside the corresponding parameter.

After the input has been tagged, the controller 10 determines whether all questions in the display patient profile have been selected (S30) if all of the questions have not been selected, the controller selects the next question (S14) and the process (S16-S30) is repeated. If all of the questions have been selected, the controller 10 accesses the database 200 and selects a treatment protocol based on the identified medical condition and/or one or more of the stored inputs (S34). For example, based on input indicating that the patient may be suffering an acute myocardial infarction, a treatment protocol for the acute myocardial infarction would be loaded and displayed on the display 61. The displayed treatment protocol will include a number of action items that require input from the user. The input may be an input such as a checkmark indicating that a task has been completed, or the input may require the entry of data such as the results of a test. When the data other than a time is input, the controller 10 may access the timer 70 and record the time at which the data was input for the purpose of determining a metric.

The controller 10 selects a first action item for which data has been received within the displayed treatment protocol (S36), and in a similar manner as above, the input judging circuit, routine, or application 15 determines whether an acceptable input was received (S38). That is, if an unacceptable input is received (S38=NO), an error is displayed and the data field is cleared (S40).

If an acceptable input is received (S38=YES), the controller 10 stores the input in the stored input portion 21 of the memory 20 (S42), the metric determining circuit, routine, or application 11 evaluates the input data and determines a relevant metric from the stored input (S44), the metric comparing circuit, routine, or application 12 accesses the database 200 and compares the determined metric with stored parameters for the particular metric (S48) and tags the stored input as being inside or outside the relevant parameters in the same manner as discussed above (S50, S52).

Next, the abnormality identifying circuit, routine, or application 13 determines whether there is any indication of an abnormality from the stored input (S54), and the protocol adjusting circuit, routine, or application 14 accesses the database 200 and determines whether the indicated abnormality alters the treatment protocol (S56). For example, as discussed above, if the stored data indicates the abnormality of a patient's blood pressure having risen after a previous protocol data entry indicated the administration of a blood-pressure-reducing medication, the protocol adjusting circuit, routine, or application 14 could adjust the protocol to account for the increased blood pressure by adjusting the protocol to include additional blood-pressure-reducing measures as part of the adjusted protocol. If the abnormality alters the treatment protocol (S56=YES), the protocol adjusting circuit, routine, or application 14 accesses the database 200 and adjusts the protocol accordingly (S58).

If the abnormality does not alter the treatment protocol (S56=NO), the controller 10 then determines whether all action items in the treatment protocol have been selected (S60), if all items have not been selected (S60=NO), the next action item including input data is selected (S36) and the process repeats (S38~S60). If all items have been selected (S60=YES), the method ends. After the method has ended, the medical treatment device may be connected to the database 200 via connector 40 or via wireless transmitter/receivers 30, 210, and the controller 10 may upload some or all of the stored data (with or without tags), including some or all of the stored metrics, to the database 200 for statistical analysis and/or to improve the patient profiles and treatment protocols stored therein.

According to the above described method, as the device is passed between caregivers as the patient profile and treatment protocols progress, each caregiver immediately knows what the patient's condition is, exactly what has been done, the timing of what has been done, and what still needs to be done. Furthermore, the device can evaluate metrics (such as timing) so that the caregiver can see whether anything occurred outside of preferable parameters. Whenever a malfunction arises, the device can adjust the protocol so that the caregivers can proceed with the proper care in a timely and efficient manner.

Figure 5:
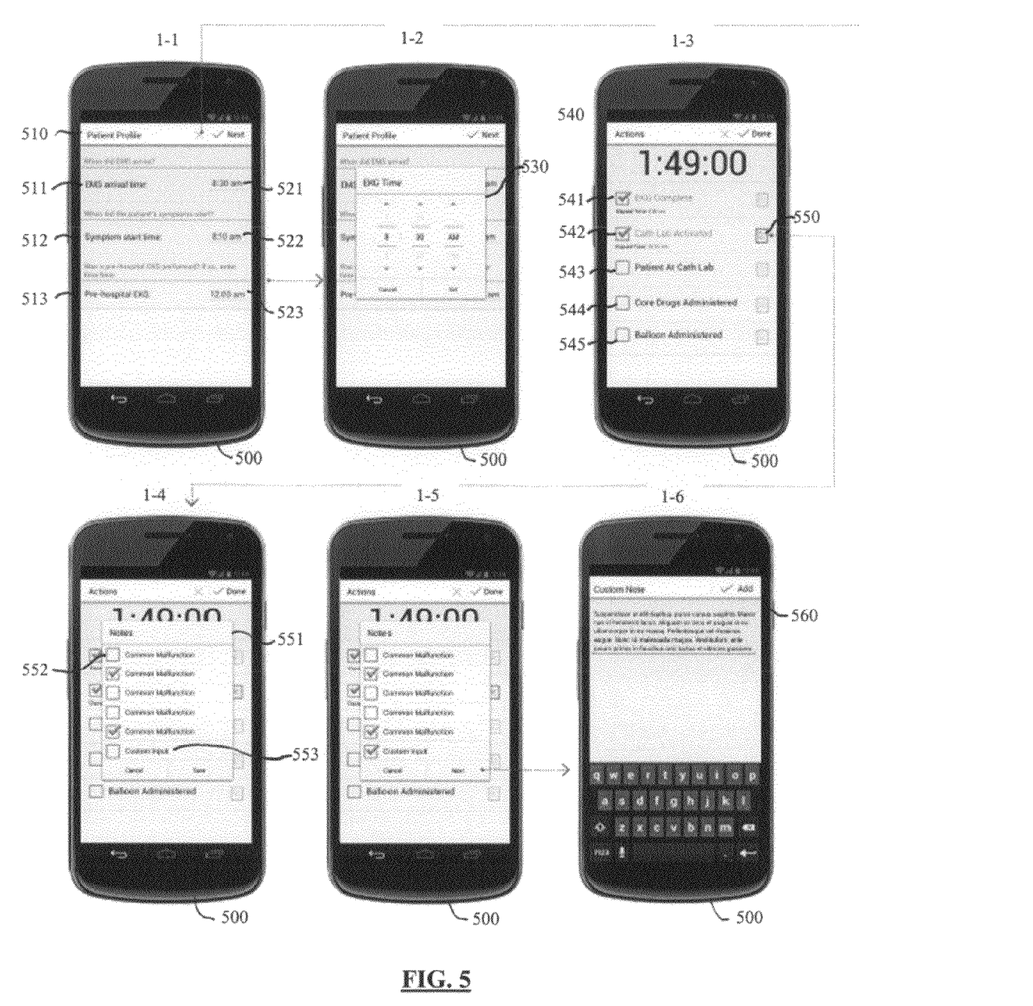
FIG. 5 includes exemplary screenshots of a medical device according to a particular implementation.

To aid in understanding, a particular exemplary implementation of the medical treatment device will be described with reference to FIG. 5. According to this implementation, the medical treatment device is implemented as a smartphone 500. On screen 1-1, initial, data has been entered, for example, by an EMT indicating that the patient has had an acute myocardial infarction, and a patient profile 510 has been downloaded from the database. Three questions 511, 512, and 513 from the patient profile 510 are displayed on the smartphone 500. In this example, each question has an area 521, 522, 523 to input a time. Screen 1-2 shows an entry window 530 that permits a time to be inputted for a particular question to reduce unacceptable input.

Based on the input times, metrics indicating how long it took for each important event (e.g., arrival at a particular place) or procedure (e.g., an EKG) to occur can be determined and compared against recommended times (parameters). When an input time falls outside a recommended interval it can be shown in red, and when an input time is within a recommended interval it can be shown in green.

Screen 1-3 shows events 541-545 associated with a treatment protocol for the acute myocardial infarction. As shown, two events 541, 542 have already been completed and three events 543-545 await completion. One hour and forty-nine minutes have elapsed. Thus, when any caregiver looks at the smartphone 500 they can easily see how long treatment has taken and exactly which events have been completed and which have not. In this example, each event has an expandable field 550 that provides more information about that particular event. For example, as shown in screen 1-4, the expanded window 551 corresponding to the field 550 for event 542 includes a list of common malfunctions 552 that might occur during that event 542. When a malfunction occurs, the caregiver can simply indicate the malfunction with a check box. This type of malfunction can be used to adjust the treatment protocol in the same way that a determined malfunction can alter the treatment protocol. As shown in screens 1-5 and 1-6 item 553 in the expanded window allows the caregiver to insert descriptive text 560.

Thus, as evidenced by this implementation, as the medical treatment device is passed between caregivers as the patient profile and treatment protocols progress, each caregiver immediately knows what the patients condition is, exactly what has been done, the timing of what has been done, and what still needs to be done. Furthermore, the device can evaluate metrics (such as timing) so that the caregiver can see whether anything occurred outside of preferable parameters. Whenever a malfunction arises, the device can adjust the protocol so that the caregivers can proceed with the proper care in a timely and efficient manner.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. A medical treatment device, comprising:
a display;
an input device; and
a controller configured to:
receive from the input device medical condition information usable to identify a medical condition;
access a database that stores patient profile information and treatment protocol information;
based on the received medical condition information, select a stored patient profile from the database;
display one or more data entry fields on the display based on the selected patient profile;
receive from the input device patient information for one of the data entry fields;
analyze the received patient information to determine a first metric;
compare the determined first metric with a corresponding first parameter;
when the determined first metric is within the corresponding first parameter, tag the patient information as being within the first parameter and display the patient information on the display in a first manner; and
when the determined first metric is outside the corresponding first parameter, tag the patient information as being outside the first parameter and display the patient information on the display in a second manner.

2. The medical treatment device of claim 1, wherein the controller is configured to store at least one of the medical condition information, patient information, and determined first metric in the database.

3. The medical treatment device of claim 1, wherein the controller is configured to:
based on at least one of the received medical condition information and the received patient information, select a stored treatment protocol from the database;
display one or more data entry fields on the display based on the selected treatment protocol;
receive from the input device treatment information for one of the data entry fields;
analyze the received treatment information to determine a second metric;
compare the determined second metric with a corresponding, second parameter;
when the determined second metric is within the corresponding second parameter, tag the treatment information as being within the second parameter and display the treatment information on the display in the first manner;
when the determined second metric is outside the corresponding second parameter, tag the treatment information as being outside the second parameter and display the treatment information on the display in the second manner; and
evaluate the treatment information to determine whether or not an abnormality exits;
when an abnormality exists, determine whether the abnormality requires that the treatment protocol be adjusted; and
when the abnormality requires that the treatment protocol be adjusted, adjust the treatment protocol.

4. The medical treatment device of claim 3, wherein the controller is configured to store at least one of the medical condition information, patient information, treatment information, determined first metric, and determined second metric in the database.

5. The medical treatment device of claim further comprising a transmitter/receiver, wherein:
the database is an external database that is separate from the medical treatment device; and
the controller is configured to access external database in at least one of the following manners:
wirelessly via the transmitter/receiver; and
by being connected with a cable.

6. The medical treatment device of claim 5, further comprising an abbreviated database, wherein the controller is configured to:
determine whether the external database can be accessed; and
when the external database cannot be accessed, select the stored patient profile from the abbreviated database based on the received medical condition information.

7. The medical treatment device of claim 6, wherein the controller is configured to:
access the external database to acquire updating information; and
update the abbreviated database with the updated information.

8. The medical treatment device of claim 5, further comprising an internal database that can be updated to include all of the patent profiles and treatment protocols stored in the external database, wherein the controller is configured to select the stored patient profile from the internal database based on the received medical condition information.

9. The medical treatment device of claim 8, wherein the controller is configured to:
   access the external database to acquire updating information; and
   update the internal database with the updated information.

10. The medical treatment device of claim 1, wherein the medical treatment device is portable and is configured to be placed on or near a patient when the patient is moved.

11. The medical treatment device of claim 10, wherein the medical treatment device is a smartphone.

12. A medical treatment method using a medical treatment device having an input device, a controller, and a display, the method comprising:
   causing the controller to receive from the input device medical condition information usable to identify a medical condition;
   causing the controller to access a database that stores patient profile information and treatment protocol information;
   causing the controller to select a stored patient profile from the database based on the received medical condition information;
   causing the controller to display one or more data entry fields on the display based on the selected patient profile;
   causing the controller to receive from the input device patient information for one of the data entry fields;
   causing the controller to analyze the received patient information to determine a first metric;
   causing the controller to compare the determined first metric with a corresponding first parameter;
   when the determined first metric is within the corresponding first parameter, causing the controller to tag the patient information as being within the first parameter and display the patient information on the display in a first manner; and
   when the determined first metric is outside the corresponding first parameter, causing the controller to tag the patient information as being outside the first parameter and display the patient information on the display in a second manner.

13. The medical treatment method of claim 12, further comprising causing the controller to store at least one of the medical condition information, patient information, and determined first metric in the database.

14. The medical treatment method of claim 12, further comprising:
   causing the controller to select a stored treatment protocol from the database based on at least one of the received medical condition information and the received patient information;
   causing the controller to display one or more data entry fields on the display based on the selected treatment protocol;
   causing the controller to receive from the input device treatment information for one of the data entry fields;
   causing the controller to analyze the received treatment information to determine a second metric;
   causing the controller to compare the determined second metric with a corresponding second parameter;
   when the determined second metric is within the corresponding second parameter, causing the controller to tag the treatment information as being within the second parameter and display the treatment information on the display in the first manner;
   when the determined second metric is outside the corresponding second parameter, causing the controller to tag the treatment information as being outside the second parameter and display the treatment information on the display in the second manner;
   causing the controller to evaluate the treatment information to determine whether or not an abnormality exits;
   when an abnormality exists, causing the controller to determine whether the abnormality requires that the treatment protocol be adjusted; and
   when the abnormality requires that the treatment protocol be adjusted, causing the controller to adjust the treatment protocol.

15. The medical treatment method of claim 14, further comprising causing the controller to store at least one of the medical condition information, patient information, treatment information, determined first metric, and determined second metric in the database.

16. The medical treatment method of claim 12, wherein:
   the medical treatment device further comprises a transmitter/receiver;
   the database is an external database that is separate from the medical treatment device; and
   the method further comprises causing the controller to access the external database in at least one of the following manners:
      wirelessly via the transmitter/receiver; and
      by being connected with a cable.

17. The medical treatment method of claim 16, wherein:
   the medical treatment device further comprises an abbreviated database; and
   the method further comprises causing the controller to:
      determine whether the external database can be accessed; and
      when the external database cannot be accessed, select, the stored patient profile from the abbreviated database based on the received medical condition information.

18. The medical treatment method of claim 17, the method further comprising:
   causing the controller to access the external database to acquire updating information; and
   causing the controller to update the abbreviated database with the updated information.

19. The medical treatment method of claim 16, wherein:
   the medical treatment device further comprises an internal database that can be updated to include all of the patent profiles and treatment protocols stored in the external database; and
   the method further comprises causing the controller to select the stored patient profile from the internal database based on the received medical condition information.

20. The medical treatment method of claim 19, wherein the method further comprises causing the controller to:
   access the external database to acquire updating information; and
   update the internal database with the updated information.

21. The medical treatment method of claim 12, wherein the medical treatment device is portable and is configured to be placed on or near a patient when the patient is moved.

22. The medical treatment method of claim 21, wherein the medical treatment device is a smartphone.

23. A computer-readable storage medium storing a computer-executable medical treatment program, the program comprising:
> instructions for receiving from the input device medical condition information usable to identify a medical condition;
> instructions for accessing a database that stores patient profile information and treatment protocol information;
> instructions for selecting a stored patient profile from the database based on the received medical condition information;
> instructions for displaying one or more data entry fields on the display based on the selected patient profile;
> instructions for receiving from the input device patient information for one of the data entry fields;
> instructions for analyzing the received patient information to determine a first metric;
> instructions for comparing the determined first metric with a corresponding first parameter;
> instructions for, when the determined first metric is within the corresponding first parameter, tagging the patient information as being within the first parameter and display the patient information on the display in a first manner; and
> instructions for, when the determined first metric is outside the corresponding first parameter, tagging the patient information as being outside the first parameter and display the patient information on the display in a second manner.

24. The computer-readable storage medium of claim 23, the program further comprising:
> instructions for selecting a stored treatment protocol from the database based on at least one of the received medical condition information and the received patient information;
> instructions for displaying one or more data entry fields on the display based on the selected treatment protocol;
> instructions for receiving from the input device treatment information for one of the data entry fields;
> instructions for analyzing the received treatment information to determine a second metric;
> instructions for comparing the determined second metric with a corresponding second parameter;
> instructions for, when the determined second metric is within the corresponding second parameter, tagging the treatment information as being within the second parameter and display the treatment information on the display in the first manner;
> instructions for, when the determined second metric is outside the corresponding second parameter, tagging the treatment information as being outside the second parameter and display the treatment information on the display in the second manner;
> instructions for evaluating the treatment information to determine whether or not an abnormality exits;
> instructions for, when an abnormality exists, determining whether the abnormality requires that the treatment protocol be adjusted; and
> instructions for, when the abnormality requires that the treatment protocol be adjusted, adjusting the treatment protocol.

* * * * *